United States Patent
Jarrell

(10) Patent No.: US 10,438,689 B2
(45) Date of Patent: Oct. 8, 2019

(54) METHOD AND SYSTEM FOR SCREENING OF CELLS AND ORGANOIDS

(71) Applicant: Waters Technologies Corporation, Milford, MA (US)

(72) Inventor: Joseph A. Jarrell, Newton Highlands, MA (US)

(73) Assignee: WATERS TECHNOLOGIES CORPORATION, Milford, MA (US)

(\*) Notice: Subject to any disclaimer, the term of this patent is extended or adjusted under 35 U.S.C. 154(b) by 73 days.

(21) Appl. No.: 15/901,353

(22) Filed: Feb. 21, 2018

(65) Prior Publication Data

US 2018/0253526 A1   Sep. 6, 2018

Related U.S. Application Data

(60) Provisional application No. 62/466,471, filed on Mar. 3, 2017.

(51) Int. Cl.
*G06K 9/00* (2006.01)
*C12Q 1/68* (2018.01)
(Continued)

(52) U.S. Cl.
CPC .......... *G16B 20/00* (2019.02); *G01N 15/1459* (2013.01); *G01N 15/1463* (2013.01);
(Continued)

(58) Field of Classification Search
USPC ........ 382/100, 103, 106–107, 128–134, 162, 382/168, 173, 181, 190, 203, 224, 232,
(Continued)

(56) References Cited

U.S. PATENT DOCUMENTS

2005/0260623 A1\* 11/2005 Trosko ................. C12Q 1/6886
435/6.11
2006/0257866 A1\* 11/2006 Welch .................... B82Y 30/00
435/6.18
(Continued)

FOREIGN PATENT DOCUMENTS

WO   2014093080 A1   6/2014

OTHER PUBLICATIONS

Masahiro Kawashima et al. "High-Resolution Imaging Mass Spectrometry Reveals Detailed Spatial Distribution of Phosphatidylinositols in Human Breast Cancer." The Official Journal of the Japanese Cancer Association, Aug. 6, 2013, vol. 104, No. 10, pp. 1372-1379.
(Continued)

*Primary Examiner* — Seyed H Azarian
(74) *Attorney, Agent, or Firm* — Schmeiser, Olsen & Watts LLP; William G. Guerin

(57) ABSTRACT

A method and apparatus for analyzing a response of a cellular entity to a component of interest are described. The cellular entity may be a cell or an organoid. The method includes processing a heterogeneous population of cellular entities that are combined with the component of interest. An entity flow containing the cellular entities is generated. A morphological image of a portion of the entity flow having a cellular entity is acquired and the cellular entity is identified as belonging to an entity class. The entity flow is provided to a mass spectrometer system that performs an analysis of the cellular entity. The mass spectrometer analysis of the cellular entity can be correlated with the identified entity class. Alternatively, portions of the entity flow are deposited as samples on a sample plate and the mass spectrometer analysis is performed offline, for example, using an ionization process with each sample.

8 Claims, 4 Drawing Sheets

(51) Int. Cl.
*G16B 20/00* (2019.01)
*G01N 15/14* (2006.01)
*G01N 33/68* (2006.01)
*G06K 9/62* (2006.01)
*G16B 40/00* (2019.01)
*G01N 33/50* (2006.01)

(52) U.S. Cl.
CPC ..... *G01N 15/1475* (2013.01); *G01N 33/5008* (2013.01); *G01N 33/5088* (2013.01); *G01N 33/6848* (2013.01); *G06K 9/00147* (2013.01); *G06K 9/6217* (2013.01); *G16B 40/00* (2019.02)

(58) Field of Classification Search
USPC ....... 382/254, 274, 276, 286–291, 305, 321; 435/6.11, 6.18; 250/288; 514/89
See application file for complete search history.

(56) References Cited

U.S. PATENT DOCUMENTS

| | | | |
|---|---|---|---|
| 2010/0227838 A1* | 9/2010 | Shah | A61K 31/454 514/89 |
| 2013/0020483 A1* | 1/2013 | Jarrell | H01L 35/34 250/288 |
| 2014/0308207 A1 | 10/2014 | Janetopoulos et al. | |
| 2016/0195466 A1 | 7/2016 | Loboda et al. | |
| 2017/0199104 A1* | 7/2017 | Gradinaru | G01N 1/30 |
| 2018/0059126 A1* | 3/2018 | Jones | A61B 90/13 |

OTHER PUBLICATIONS

Dmitry R. Bandura, et al. "Mass Cytometry: Technique for Real Time Single Cell Multitarget Immunoassay Based on Inductively Coupled Plasma Time-of-Flight Mass Spectrometry." Analytical Chemistry, Aug. 15, 2009, vol. 81, No. 16, pp. 6813-6822.

Giorgia Quadrato et al. "The Promises and Challenges of Human Brain Organoids as Models of Neuropsychiatric Disease." Nature Medicine, Nov. 2016, vol. 22, No. 11, pp. 1-9.

Farah Virani et al. "Mass Cytometry: An Evolution in ICP-MS Enabling Novel Insights in Single-Cell Biology." Spectroscopy, May 1, 2015, Issue 11, 9 pages.

Tai Rao et al. "Pharmacokinetic Study Based on a Matrix-assisted laser Desorption/Ionization Quadrupole Ion Trap Time-of-Flight Imaging Mass Microscope Combined with a Novel Relative Exposure Approach: A Case of Octreotide in Mouse Target Tissues." Analytical Chimica Acta, Dec. 3, 2016, vol. 952, pp. 71-80.

International Search Report and Written Opinion for PCT Application No. PCT/US2018/018947, dated Apr. 26, 2018.

Reka A. Otvos et al. "Development of an Online-Cell-Based Bioactivity Screening Method by Couling Liquid Chromatography to Flow Cytometry with Parallel Mass Spectrometry." Analytical Chemistry, Apr. 5, 2016, vol. 88, pp. 4825-4832.

Zach B. Bjornson et al. "Single Cell Mass Cytometry for Analysis of Immune System Functional States." National Institute of Health, Curr Opin Immunol., Aug. 2013, vol. 25, No. 4, pp. 1-18.

Anne E. Carpenter, et al. "CellProfiler: Imagine Analysis Software for Identifying and Qualifying Cell Phenotypes." Genome Biology, Oct. 31 2006, vol. 7, issue 10, 11 pages.

* cited by examiner

METHOD AND SYSTEM FOR SCREENING OF CELLS AND ORGANOIDS

RELATED APPLICATIONS

This application claims the benefit of U.S. Provisional Application No. 62/466,471, filed on Mar. 3, 2017, and titled "METHOD AND SYSTEM FOR SCREENING OF CELLS AND ORGANOIDS," the entirety of which is incorporated by reference herein.

FIELD OF THE INVENTION

The invention relates generally to real-time analysis of cell and organoid morphology. More particularly, the invention relates to a method and apparatus that enable a heterogeneous cell or organoid population to be used for rapid evaluation of how a compound affects a particular human organ or for drug screening processes.

BACKGROUND

In drug development activities, efficacy studies are typically performed before a candidate drug is evaluated for toxicity. A drug may combine with a known receptor and demonstrate some biochemical reaction at the cell level. Efficacy studies are generally performed in advance of clinical evaluation on humans where the drug may be deemed unsatisfactory due to toxic effects. Thus substantial investments of cost and time occurring prior to human clinical trials may be at risk.

Organoids are three-dimensional miniaturized versions of an organ that can be produced in vitro. Organoids may be produced from one or more stem cells that organize into larger cell organizations based on the self-renewal and differentiation capabilities of the stem cells. If the organoids are sufficiently similar to a corresponding human organ in terms of susceptibility to a drug candidate, it may be possible to evaluate the response of similar organoids in parallel with the main efficacy process. For example, drug discovery processes for neurological diseases or states can be correlated with the degree of neurotransmitter synthesis. The process may look for candidates that combine with a receptor to change or modulate the generation of these neurotransmitters based on knowledge about the disease. The ability to generate appropriate clumps of cells for this purpose is difficult. Researchers want to generate homogeneous populations of organoids that correspond to a specific portion of the brain; however, efforts generally only result in the generation of heterogeneous populations representing multiple regions of the brain.

SUMMARY

In one aspect, the invention features a method of analyzing a response of a cellular entity to a component of interest. The method includes generating an entity flow including a serial flow of cellular entities in a solution from a source of a heterogeneous population of the cellular entities combined with the component of interest. The heterogeneous population includes a plurality of entity classes. A morphological image of a portion of the entity flow having a cellular entity is acquired. The morphological image is analyzed to determine an entity class, from the plurality of entity classes, associated with the cellular entity. The entity flow is provided to a mass spectrometer system and a mass spectrometer analysis of the cellular entity is performed. The mass spectrometer analysis of the cellular entity is associated with the entity class determined for the cellular entity.

The cellular entity may be a single cell or an organoid, and the plurality of entity classes may be a plurality of cell classes or a plurality of organoid classes. In one embodiment, providing the entity flow to a mass spectrometer system includes depositing a sample containing the cellular entity onto a sample plate and the mass spectrometer analysis is an offline analysis performed on the sample.

In another aspect, the invention features a system for analyzing a response of a cellular entity to a component of interest. The system includes a flow channel, a morphological imaging system, a processor and a mass spectrometer. The flow channel is configured to receive an entity flow that includes a serial flow of cellular entities in a solution from a source of a heterogeneous population of the cellular entities combined with the component of interest. The heterogeneous population includes a plurality of entity classes. The morphological imaging system is in optical communication with the flow channel and is configured to acquire a morphological image of a portion of the entity flow having a cellular entity. The processor is in communication with the morphological imaging system to receive image data from the morphological imaging system. The processing system is configured to determine an entity class from the plurality of entity classes for the cellular entity. The mass spectrometer is in communication with the morphological imaging system and in fluid communication with the flow channel to receive the entity flow. The mass spectrometer is configured to perform a mass spectrometer analysis of the cellular entity and the processor is further configured to associate the mass spectrometer analysis of the cellular entity with the entity class determined for the cellular entity.

The system may further include a mass spectrometer interface in fluid communication with the flow channel to receive the entity flow and in further communication with the mass spectrometer to provide an ionized entity flow to the mass spectrometer. The cellular entity may be a single cell or an organoid, and the plurality of entity classes may be a plurality of cell classes or a plurality of organoid classes.

In still another aspect, the invention features a system for analyzing a response of a cellular entity to a component of interest. The system includes a flow channel, a morphological imaging system, a processor and a deposition module. The flow channel is configured to receive an entity flow that includes a serial flow of cellular entities in a solution from a source of a heterogeneous population of the cellular entities combined with the component of interest. The heterogeneous population includes a plurality of entity classes. The morphological imaging system is in optical communication with the flow channel and is configured to acquire a morphological image of a portion of the entity flow having a cellular entity. The processor is in communication with the morphological imaging system to receive image data from the morphological imaging system. The processing system is configured to determine an entity class from the plurality of entity classes for the cellular entity. The deposition module is in fluid communication with the flow channel to receive the entity flow and to generate, for each of the cellular entities in the morphological images, a spatially-separated deposition of the cellular entity on a sample plate. The processor is further configured to associate the entity class for each of the cellular entities with a corresponding one of the spatially-separated depositions on the sample plate.

The cellular entity may be a single cell or an organoid, and the plurality of entity classes may be a plurality of cell classes or a plurality of organoid classes.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Figure 1:
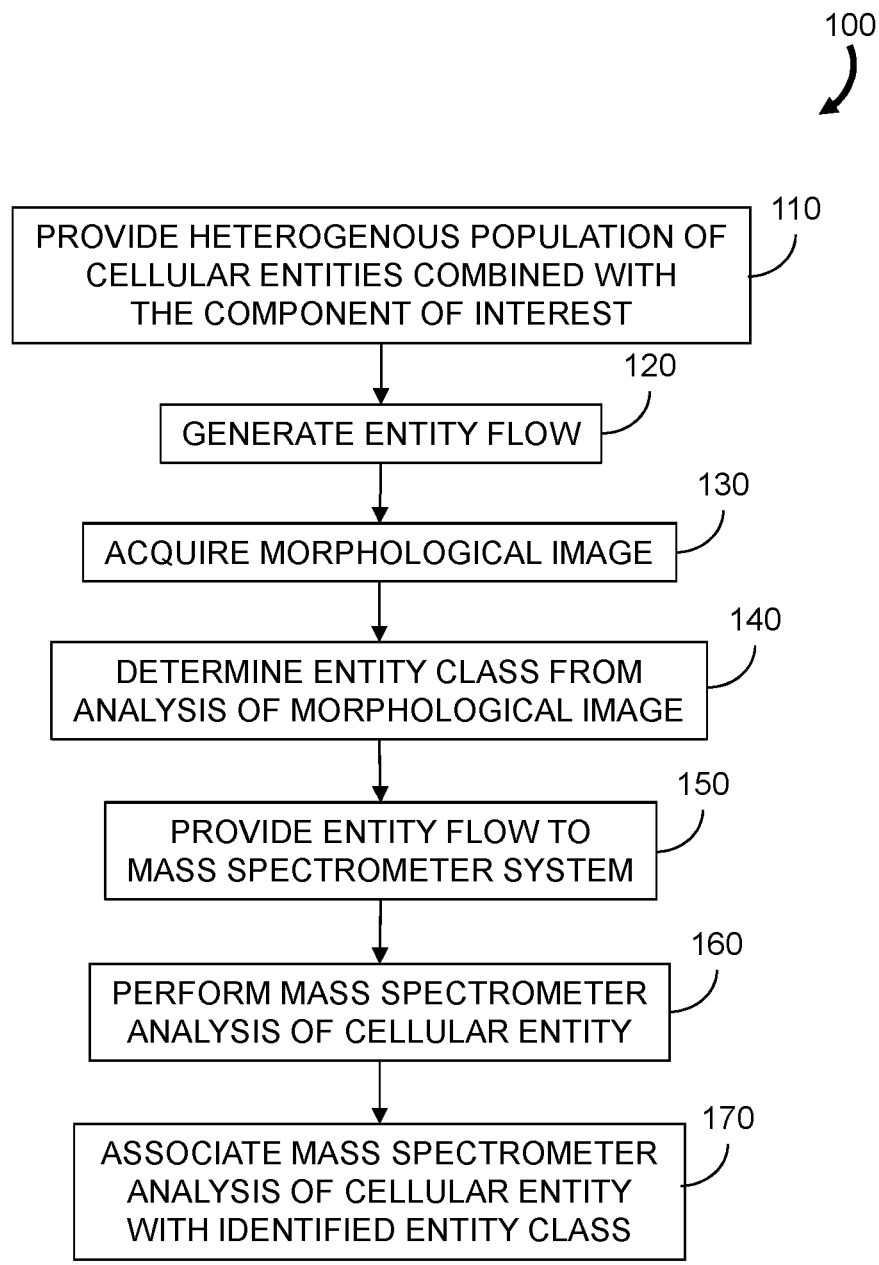
FIG. 1 is a flowchart representation of an embodiment of a method for analyzing a response of a cellular entity to a component of interest.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure.

As used herein, a "cellular entity" means a cell or a cluster of similar cells, such as an organoid. As used herein, an "organoid" is a three-dimensional miniaturized version of an organ that can be produced in vitro from one or more stem cells that organize into larger cell organizations and which mimic some properties of a particular human organ. Organoids may be used for screening new drug candidates as the receptors on the cells of organoids often behave more like the receptors on the cells of the corresponding human organs than the receptors on the cells of animal models.

In various embodiments below, an apparatus and method for analyzing a response of a cellular entity to a component of interest are described. A "component of interest" means a compound or substance, such as a candidate drug compound, that is evaluated based on the response of a cellular entity to the component. The method includes processing a heterogeneous population of cellular entities that are combined with the component of interest. An entity flow of a solution containing the cellular entities is generated. A morphological image of a portion of the entity flow having a cellular entity is acquired and the cellular entity is identified as belonging to one of a plurality of entity classes (cell classes or organoid classes). By way of a specific example, the entity classes may be organoid classes for brain organoids and may include midbrain organoids, cerebellar organoids and hippocampal organoids. The entity flow is provided to a mass spectrometer system where a mass spectrometer analysis of the cellular entity is performed. The mass spectrometer analysis of the cellular entity can be correlated with the identified entity class.

A morphological image may be an optical image from which the shape of a cellular entity may be determined. The optical image may be a digital image acquired with optical imaging components and a digital imager. An image processing algorithm can be applied to the digital images to determine if the cellular entity in the digital image is within a size range associated with a particular entity class. By way of a simple numerical example, a maximum detected dimension of a cellular entity within an image may be compared to a minimum value and a maximum value associated with a particular entity class. For example, if the cellular entity is an organoid and organoids in one organoid class have a typical maximum dimension between 450 um and 550 um, an organoid having a maximum detected dimension of 530 μm would be identified as belonging to the organoid class as long as there are no other organoid classes in the organoid population having an overlapping dimensional range. Alternatively, or in addition, a shape characterization of a cellular entity in a digital image can be made and compared to a shape characterization of an entity class. Image analysis and classification can be implemented using commercially-available software or open source software (e.g., CellProfiler cell image analysis software available from cellprofiler.org). Alternatively, a morphological image can be a "spectral image" of the light emitted from a fluorescent probe on a cellular entity that is associated with the binding of the component of interest. If a single fluorescent probe is used, a detection of the emitted fluorescent light can mean that the cellular entity is in the class of interest. If multiple distinct fluorescent probes are used for determining multiple classes of entities, a spectral characteristic of the emitted fluorescent light from a cellular entity can be used to determine its entity class from the multiple detectable entity classes.

FIG. 1 is a flowchart representation of an embodiment of a method 100 for analyzing a response of a cellular entity to a component of interest. The method includes providing (110) a heterogeneous population of cellular entities combined with a component of interest. For example, the cellular entities may be organoids and the component of interest may be a drug compound to be evaluated with respect to organoids of a single classification contained within the heterogeneous population. An entity flow is generated (120) from the heterogeneous population of cellular entities, for example, by injecting the population into a liquid that is compatible with at least one entity class of interest. Morphological images of portions of the entity flow are acquired (130) and analyzed to determine (140) an entity class for a cellular entity that may be present in the flow portion. The entity flow is provided (150) to a mass spectrometer system where an analysis is performed (160). The results of the analysis may relate to the effect of the component of interest on the cellular entities.

The entity class identified based on the morphological image analysis may be associated (170) with the mass spectrometry analysis for the same cellular entity. For example, the timing of the morphological image acquisition may be "synchronized" with the subsequent mass spectrometry analysis associated with the morphological image based on a predetermined delay time. Alternatively, an observable marker may be injected into the entity flow at a known location relative to a classified organoid and detected downstream to reduce or eliminate reliance on timing. Thus a subset of the mass spectrometry measurements performed on the heterogeneous population may be examined to determine the effect of the compound of interest on an entity class.

In an alternative embodiment of the method, providing the entity flow to the mass spectrometer system includes depositing portions of the entity flow as samples on a sample plate and the mass spectrometer analysis is performed offline, for example, using an ionization process with each of the samples.

Advantageously, the method eliminates the need to generate a homogeneous entity population, that is, a population of cellular entities belonging to only one entity class. Thus the effect of the compound with respect to a single entity class may be extracted from the mass spectrometer data acquired for the entire heterogeneous population. Moreover, the real-time morphological analysis enables evaluation of multiple entity classes from a single analysis run when the morphological images allow for identification of multiple entity classes.

Figure 2:
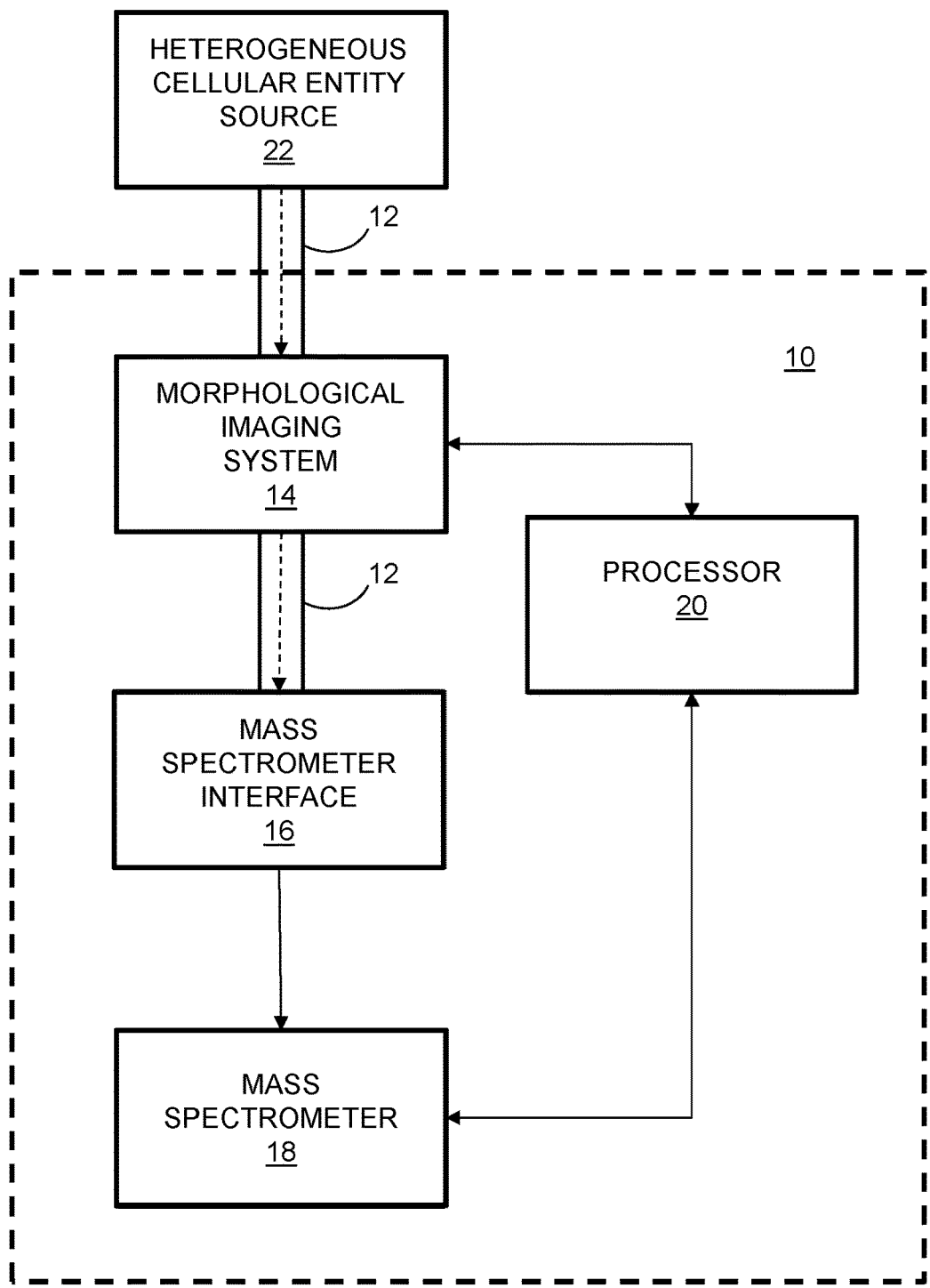
FIG. 2 is a functional block diagram of an embodiment of a system for analyzing a response of a cellular entity to a component of interest.

FIG. 2 is a functional block diagram of an embodiment of a system 10 for analyzing a response of a cellular entity to a component of interest. This online system 10 includes a flow channel 12, a morphological imaging system 14, a mass spectrometer interface 16, a mass spectrometer 18 and a processor 20. The system 10 receives an entity flow (e.g., a flow of cells or organoids) through a flow channel 12. The entity flow includes a serial flow of cellular entities from a source 22 of heterogeneous cellular entities. As used herein, a serial flow means that substantially only one cellular entity may pass a location along the flow channel 12 at a given time. A more concentrated flow of cellular entities may be used, but the quality of the data may degrade. The cross-sectional area of the flow channel 12 may be limited in size to achieve the desired serial flow without clogging. For example, if the flow channel is a tube having a circular cross-section, the inner diameter of the tube may be less than twice a nominal dimension of the cellular entities passing through the flow channel. If the cellular entities are individual cells, the inner diameter is therefore not substantially greater than the nominal dimension of the individual cells. In contrast, if the cellular entities are organoids, the inner diameter is generally substantially greater; however, the inner diameters remains limited to a value that is not substantially greater than the nominal dimension of the organoid. Additionally, the concentration of organoids in the organoid flow may be controlled to further reduce the opportunity for two organoids to pass by a single location in the flow channel 12 at the same time.

The flow channel 12 may be formed from a variety of materials. At least a portion of the flow channel 12 is formed from an optically transparent material to permit illumination and imaging of a portion of the entity flow. In one example, the flow channel 12 is formed of quartz.

The source 22 of heterogeneous cellular entities may be a reservoir holding a solution containing the cellular entities. Alternatively, the source 22 may be a Petri dish or similar container from which the heterogeneous cellular entities are removed and introduced into a flow of a liquid that is compatible with the cellular entities.

The morphological imaging system 14 is configured to acquire a morphological image of a portion of the entity flow through a transparent wall of the fluid channel 12. The morphological imaging system 14 may include one or more light sources used to illuminate the portion of the entity flow and one or more imaging lenses (e.g., microscope objectives) to form an image of the entity flow on one or more imaging detectors as described in more detail below. The light sources may be high intensity light sources that are pulsed or otherwise modulated to provide illumination at a pulse rate that enables consecutive portions of the entity flow to be imaged. Alternatively, continuous light sources of sufficient intensity may be used. For example, the light sources may be lasers, laser diodes or pulsed light emitting diodes (LEDs). The morphological imaging system 14 may also include imaging processing capability to enable a shape-based analysis of any cellular entity present in an image. Alternatively, the acquired images may be provided to the processor 20 which can process the digital images and perform the shaped-based analysis.

In an alternative configuration utilizing fluorescent probes to classify the cellular entities, the light sources in the morphological imaging system 14 are adapted for emitting one or more excitation wavelengths. The lenses and their corresponding detectors are configured to sense one or more fluorescence spectra emitted by cellular entities having fluorescent probes. The different fluorescence spectra that may be detected correspond to different classes of cellular entities present in the organoid flow.

The mass spectrometer interface 16 receives the serial flow of heterogeneous cellular entities after exiting the fluid channel 14 and ionizes the flow before it is provided to the mass spectrometer 18. The mass spectrometer interface 16 may utilize any one of a number of ionization techniques known in the art. For example, the mass spectrometer interface 16 may utilize an electrospray ionization. A liquid that causes the individual cells or the cells of the organoid to lyse may be introduced into the flow upstream from the mass spectrometer interface 16. For example, the fluid channel 12 may include a fluidic tee where the lysing agent is introduced. In alternative examples, the mass spectrometer interface 16 may ionize the flow with an inductively coupled plasma (ICP), laser ablation or an RF discharge. The mass spectrometer 18 receives the ionized flow and performs a mass spectrometer analysis.

The processor 20 receives the morphological image data from the imaging system. In one embodiment, the morphological image data includes two dimensional image data that are analyzed by the processor 20 for shape and/or size to classify a cellular entity in the image. In another embodiment, the morphological image data are spectral fluorescence data that are analyzed by the processor 20 to determine the entity class. Alternately, shape, size and fluorescent data may be acquired simultaneously or nearly simultaneously. In alternative embodiments, the morphological imaging system 14 may include image processing and classification capabilities such that the entity classifications are provided by the morphological imaging system 14 to the processor 20.

The processor 20 "associates," or correlates, the mass spectrometer analyses with the entity classifications. More specifically, the entity classification for a morphological image of a cellular entity is associated with the mass spectrometer analysis of that cellular entity. Thus the mass spectrometer data for an entity class may be identified from a larger data set of all mass spectrometer measurement data.

The association of the organoid classification with the mass spectrometer analysis may be accomplished by determining a time delay between the time of acquisition of the morphological image and the time that the mass spectrometer analyzes the cellular entity in the morphological image. Knowledge of the flow rate and the dimensions of the flow channel 12 may be used to calculate the time delay. Alternatively, the time delay can be experimentally established by standard processes for determining flow rates such as monitoring the flow of microscopic plastic beads through the flow path or injecting bubbles or droplets of gas or other fluids into the flow path.

Figure 3A:
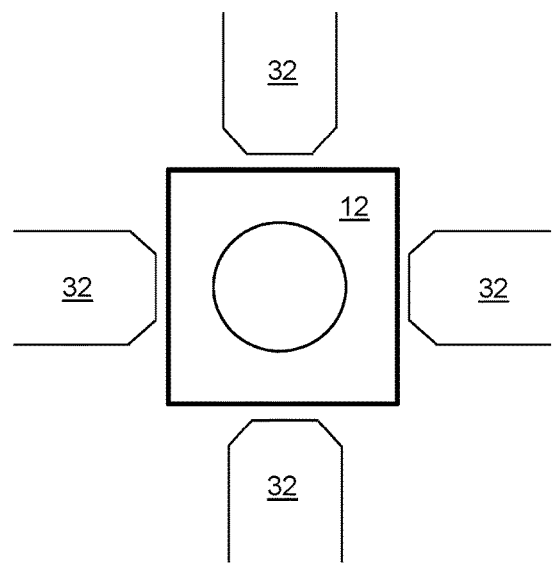
FIG. 3A is a block diagram depicting one configuration of a morphological imaging system that may be used to acquire morphological images of portions of a flow of cells or organoids.

FIG. 3A shows one configuration of a morphological imaging system that may be used to acquire morphological images of portions of the entity flow. Four microscope objectives 32 are arranged in a plane orthogonal to the direction of the organoid flow through the flow channel 12 and allow for multiple simultaneous images, either shape images or spectral images, to be acquired.

For shape-based analysis, multiple images may be acquired simultaneously from the objectives 32 for morphological characterization. Optionally, at least one of the objectives 32 may be used as a condenser to illuminate the portion of the fluid channel being images by the other objectives 32. In an alternative mode of operation, the images from the different objectives 32 may be acquired at different times and synchronized to enable rapid image acquisition for the morphological characterization. Alternatively, images may be acquired simultaneously from multiple objectives, with each objective also simultaneously serving as a condenser if each objective is used to acquire images comprising different wavelengths.

For fluorescence imaging, two or more of the microscope objectives 32 may be used as condensers with excitation sources having similar or different excitation wavelengths to illuminate the portion of the fluid channel. One or more types of continuous or pulsed or modulated light sources may be used, such as lasers, laser diodes and/or LEDs. At least one objective 32 is used to receive light emitted from any cellular entity passing through the channel portion and to provide the received light to a device or system that generates a spectral image of the emitted light. The spectral image may include a characterization of the emission spectrum of the emitted light, for example, as a nominal wavelength or wavelength band that can be associated with one or more types of fluorescent probes used for entity classification. The device or system used to generate the spectral image may be synchronized with respect to the pulses of the excitation optical energy. For example, the detection of fluorescent light may be deactivated during the excitation time and activated after the termination of excitation for a duration based on known fluorescence characteristics for the fluorescent probes.

Figure 3B:
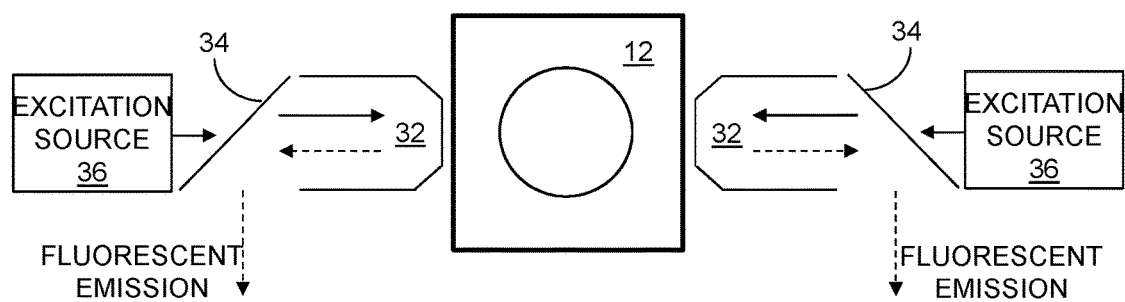
FIG. 3B is a block diagram of another configuration of a morphological imaging system that may be used to acquire morphological images of portions of a flow of cells or organoids.

FIG. 3B shows a block diagram of an imaging system that includes excitation sources 36, optical filters 34 and a pair of microscope objectives 32 that also perform as condensers. Each excitation source 36 emits optical energy having an excitation spectrum, which in the case of lasers or laser diodes, is a narrow excitation spectrum. The excitation spectra may be the same or different from each other. Optical energy emitted by each source 36 passes through an optical filter 34, such as a dichroic filter, lowpass filter or highpass filter, that passes the optical energy in a wavelength band that includes the source wavelengths and reflects optical energy outside the wavelength band. Thus light emitted from fluorescent probes on the cellular entities that is at different wavelengths than the source excitation and collected by the objective 32 is reflected from the optical filter 34 to an optical radiation detector (not shown). Fluorescent probes with different emission spectra may be used. By using dichroic filters having different transmission bands, each matching the emission spectrum of a different probe, it is possible to simultaneously detect more than one probe. The fluorescent light captured by an objective 32 can thus be analyzed to determine its spectral characteristics which in turn can be associated with a particular fluorescent probe and entity class.

Although FIGS. 3A and 3B depicts specific numbers and arrangements of microscope objectives 32, it will be recognized that other numbers and arrangements of objectives may be used. The number of objectives used may depend on the required optical resolution desired. High resolution images typically require large numerical aperture imaging systems. Four to six objectives may be sufficient for a range of applications.

Figure 4:
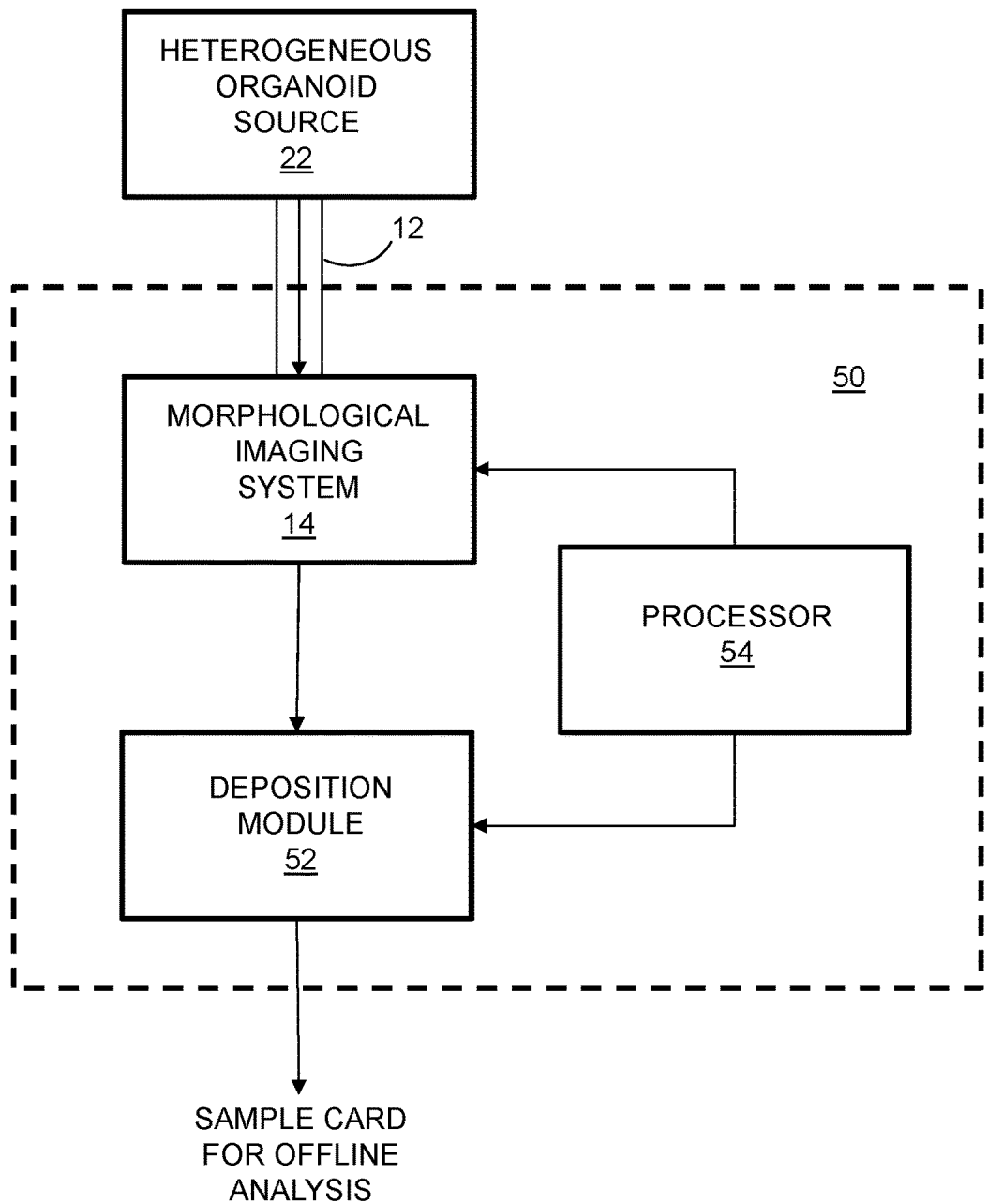
FIG. 4 is a functional block diagram of another embodiment of a system for analyzing a response of a cellular entity to a component of interest.

FIG. 4 is a functional block diagram of another embodiment of a system 50 for analyzing a response of a cellular entity to a component of interest. This offline system 50 includes a flow channel 12, a morphological imaging system 14 a sample deposition module 52 and a processor 54. The flow channel 12 and morphological imaging system 14 may be similar to the counterpart components described above with respect to the system 10 of FIG. 2; however, instead of conducting the entity flow to a mass spectrometer system, the entity flow is directed to the sample deposition module 52 where it is modulated into a matrix for deposition into a geometric spot pattern on a sample plate.

In one example, if the entity flow is a flow of organoids, detected organoids are deposited at indexed locations on the sample plate with the processor 54 associating each deposited spot on the sample plate with an organoid class. The sample plate can subsequently be transported "offline" to an ionization system (not shown), such as a matrix assisted laser desorption/ionization (MALDI) system, where each deposited spot on the sample plate may be ionized which in turn ionizes components of the spot to allow analysis by mass spectrometry. Advantageously, mass spectrometry analysis may be performed on a single class of organoids by ionizing only those samples on the sample plate belong to the organoid class of interest. Alternatively, more than one class of organoids may be analyzed without requiring that all the sample deposits be ionized. In another alternative configuration, the sample deposition module 52 may only make sample deposits for those portions of the organoid flow known to have an organoid belonging to an organoid class of interest.

While the invention has been shown and described with reference to specific preferred embodiments, it should be understood by those skilled in the art that various changes in form and detail may be made therein without departing from the scope of the invention as defined by the following claims

What is claimed is:

1. A method of analyzing a response of a cellular entity to a component of interest, the method comprising:
   generating an entity flow comprising a serial flow of cellular entities in a solution from a source of a heterogeneous population of the cellular entities combined with the component of interest, the heterogeneous population including a plurality of entity classes;
   acquiring a morphological image of a portion of the entity flow having a cellular entity;

analyzing the morphological image to determine an entity class, from the plurality of entity classes, associated with the cellular entity;
providing the entity flow to a mass spectrometer system;
performing a mass spectrometer analysis of the cellular entity; and
associating the mass spectrometer analysis of the cellular entity with the entity class determined for the cellular entity,
wherein the cellular entity is an organoid and wherein the plurality of entity classes comprises a plurality of organoid classes.

2. The method of claim 1 further comprising combining a flow of a lysing agent to the entity flow prior to performing the mass spectrometer analysis.

3. The method of claim 1 wherein providing the entity flow to a mass spectrometer system comprises depositing a sample containing the cellular entity onto a sample plate and wherein the mass spectrometer analysis is an offline analysis performed on the sample.

4. The method of claim 3 wherein performing the mass spectrometer analysis includes performing an ionization process on the deposited sample.

5. The method of claim 1 wherein analyzing of the morphological image comprises performing a shape-based analysis of the cellular entity.

6. The method of claim 1 wherein acquiring a morphological image of a portion of the entity flow includes illuminating the portion of the entity flow with an excitation source and wherein the analyzing of the morphological image includes performing a fluorescence-based analysis.

7. A system for analyzing a response of a cellular entity to a component of interest, comprising:
a flow channel to receive an entity flow comprising a serial flow of cellular entities in a solution from a source of a heterogeneous population of the cellular entities combined with the component of interest, the heterogeneous population including a plurality of entity classes;
a morphological imaging system in optical communication with the flow channel and configured to acquire a morphological image of a portion of the entity flow having a cellular entity;
a processor in communication with the morphological imaging system to receive image data therefrom, the processing system configured to determine an entity class, from the plurality of entity classes, for the cellular entity; and
a mass spectrometer in communication with the morphological imaging system and in fluid communication with the flow channel to receive the entity flow, the mass spectrometer configured to perform a mass spectrometer analysis of the cellular entity,
wherein the processor is further configured to associate the mass spectrometer analysis of the cellular entity with the entity class determined for the cellular entity,
wherein the cellular entity is an organoid and wherein the plurality of entity classes comprises a plurality of organoid classes.

8. A system for analyzing a response of a cellular entity to a component of interest, comprising:
a flow channel to receive an entity flow comprising a serial flow of cellular entities in a solution from a source of a heterogeneous population of the cellular entities combined with the component of interest, the heterogeneous population including a plurality of entity classes;
a morphological imaging system in optical communication with the flow channel and configured to acquire a morphological image of a portion of the entity flow having a cellular entity;
a processor in communication with the morphological imaging system to receive image data therefrom, the processing system configured to determine an entity class, from the plurality of entity classes, for the cellular entity; and
a deposition module in fluid communication with the flow channel to receive the entity flow and to generate, for each of the cellular entities in the morphological images, a spatially-separated deposition of the cellular entity on a sample plate,
wherein the processor is further configured to associate the entity class for each of the cellular entities with a corresponding one of the spatially-separated depositions on the sample plate,
wherein the cellular entity is an organoid and wherein the plurality of entity classes comprises a plurality of organoid classes.

* * * * *